(12) United States Patent
Van Der Puy et al.

(10) Patent No.: US 7,473,810 B1
(45) Date of Patent: Jan. 6, 2009

(54) METHOD OF DECHLORINATING ORGANIC COMPOUNDS COMPRISING VICINAL CHLORIDES

(75) Inventors: Michael Van Der Puy, Amherst, NY (US); Jingji Ma, West Seneca, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/871,348

(22) Filed: Oct. 12, 2007

(51) Int. Cl.
*C07C 19/08* (2006.01)
*C07C 17/25* (2006.01)
*C07C 17/10* (2006.01)

(52) U.S. Cl. .................. 570/230; 570/155; 570/156; 570/134; 570/153; 570/226

(58) Field of Classification Search ............... None
See application file for complete search history.

(56) References Cited

U.S. PATENT DOCUMENTS

| | | | |
|---|---|---|---|
| 2,697,124 A | 12/1954 | Mantell | |
| 2,785,984 A | 3/1957 | Kenaga | |
| 2,917,558 A | 12/1959 | Cunningham et al. | |
| 3,865,885 A | 2/1975 | Bruce | |
| 3,878,257 A | 4/1975 | Bruce | |
| 5,498,794 A | * 3/1996 | Schach et al. | 564/417 |
| 5,663,464 A | * 9/1997 | Okamoto et al. | 570/175 |
| 5,714,655 A | 2/1998 | Yamamoto et al. | |

FOREIGN PATENT DOCUMENTS

| | | |
|---|---|---|
| JP | 04002147 | 1/1992 |
| JP | 04013638 | 1/1992 |
| JP | 9061812 | 3/1997 |
| JP | 9061813 | 3/1997 |
| JP | 09278685 | 10/1997 |

OTHER PUBLICATIONS

Paleta et al., Bulletin de la Societe Chimique de France (1986), (6), 920-4.*
Okazaki et al., J. Fluorine Chem., vol. 57, p. 191 (1992).
Mori et al., "Hydrodechlorination of 1,1,2-trichloro-1,2,2-trifluorethane (CFC-113) over supported ruthenium and other noble metal catalysts," Catalysis Today, vol. 88, pp. 111 (2004).
Henne, A. L. et al., J. Am. Chem. Soc., vol. 63, pp. 3478 (1941).
Paleta, O. et al., Bull. Soc. Chim. Fr., vol. 6, pp. 920 (1986).

* cited by examiner

*Primary Examiner*—Karl J Puttlitz
(74) *Attorney, Agent, or Firm*—Erika S. Wilson

(57) ABSTRACT

Provided is a method for selectively preparing 2-chloropentafluoropropene comprising catalytic dechlorination of 1,2,2-trichloro-1,1,3,3,3-pentafluoropropane in the presence of hydrogen and a noble metal catalyst. Also provided is method for dechlorinating a vicinal chloride substituted organic compound using a palladium/barium sulfate catalyst.

11 Claims, No Drawings

METHOD OF DECHLORINATING ORGANIC COMPOUNDS COMPRISING VICINAL CHLORIDES

BACKGROUND

1. Field of Invention

The present invention relates to methods for dechlorinating organic compounds. More particularly, the invention relates to catalytic dechlorination of organic compounds comprising vicinal chlorides.

2. Description of Related Art

The compound 2-chloro-pentafluoropropene is useful as a soil fumigant (see, e.g., U.S. Pat. No. 2,785,984 (Kenaga)). Certain other soil fumigants, such as methyl bromide, are being phased out of commercial use due to their high ozone depletion potential.

Methods of preparing 2-chloro-pentafluoropropene are known. For example, U.S. Pat. No. 3,878,257 (Bruce) discloses the catalytic conversion of a propene, namely 1,1,2-trichlorotrifluoropropene-1, in the presence of HF and an anhydrous chromium (III) oxide catalyst with a divalent zinc ion to produce 2-chloro-pentafluoropropene. Although this method purportedly results in a conversion of 95-100 percent with a yield of 80 percent, it would be beneficial to produce 2-chloro-pentafluoropropene from more readily available starting materials, such as halogenated alkyls.

U.S. Pat. No. 2,917,558 (Cunningham, et al.) describes a method for producing 2-chloro-pentafluoropropene by zinc reduction of 1,2,2,3-tetrachloro-1,1,3,3-tetrafluoropentane to form a chloro-fluoropropene intermediate which is then treated with $SbF_3$ to arrive at the intended product. Preparation of olefins via the dechlorination of organic compounds containing vicinal chlorines using elemental zinc is widely used today. However, this process is disadvantageous in that is generates a large amount of waste material as it utilizes an organic solvent and generates large quantities of zinc chloride as a by product. In addition, the process disclosed in Cunningham, et al. results in low yields of $CF_3CCl=CCl_2$ (i.e., only 27-29%). As a consequence, there has been some effort to find catalytic methods for the conversion of chlorofluoroalkyls to chlorofluoroalkenes.

Others have described reactions involving the catalytic dechlorination of chlorofluoroalkyls to produce hydrofluoroalkenes. For example, U.S. Pat. No. 2,697,124 (Mantell) discloses the catalytic dechlorination of certain chlorofluorocarbons, including 1,2-dichloro-1,1,3,3,3-pentafluoropropane and 1,1,2-trichloro-2,3,3,3-tetrafluoropropane, to produce an unsaturated product that retains substantially all fluorine atoms originally present in the reactant. Likewise, U.S. Pat. No. 5,714,655 (Yamamoto, et al.) discloses that 2,2,3-trichloro-1,1,1,3,3-pentafluoropropane and at least 4.5 equivalent parts of hydrogen in the presence of a noble metal catalyst and in the vapor phase will undergo a hydrogenation reaction to form 1,1,1,3,3-pentafluoropropane.

There remains, however, a need for an economical and environmentally friendly means of preparing 2-chloropentafluoropropene directly from a catalytic dechlorination of a chlorofluorocarbon. The present invention satisfies these needs among others.

SUMMARY OF INVENTION

Applicants have found an economical and environmentally sound method for synthesizing 2-chloropentafluoropropene via the catalytic dechlorination of 2,2,3-trichloro-1,1,1,3,3-pentafluoropropane. More particularly, applicants have found that a method of catalytic dechlorination of $CF_3CCl_2CF_2Cl$ with hydrogen that proceeds with good conversion and selectivity for $CF_3CCl=CF_2$ in the presence of noble metal catalysts, such as Pd or Pt, supported on certain metallic substrates. Applicants also unexpected found that while metallic supports produce the desired product at acceptable levels (e.g., conversion of $\geq 90\%$ and selectivity $\geq 80\%$), the same catalysts supported by carbon substrates do not give the desired results. Applicants still further found that this reaction can proceed at temperatures well below 200° C. and still result in high conversion and selectivity.

Accordingly, provided is a method for selectively preparing 2-chloropentafluoropropene comprising catalytic dechlorination of 1,2,2-trichloro-1,1,3,3,3-pentafluoropropane. Preferably, the catalytic dechlorination comprises reacting 1,2,2-trichloro-1,1,3,3,3-pentafluoropropane with hydrogen in the presence of a noble metal catalyst, such as palladium, platinum, and rhodium, supported on a metal oxide or barium sulfate, to produce the 2-chloropentafluoropropene. Applicants have found that this method results in a 1,2,2-trichloro-1,1,3,3,3-pentafluoropropane conversion of $\geq 90\%$ and a selectivity for 2-chloropentafluoropropene of $\geq 80$ mol. %.

Applicants have also found that a palladium catalyst supported on a barium sulfate substrate, with or without additional material in the support, can be used to catalytically dechlorinate vicinal chlorides on organic compounds.

Therefore, also provided herein is a method for reducing the number of chlorine atoms covalently bonded to an organic compound comprising the step of reacting a vicinal chloride substituted organic compound with hydrogen in the presence of a palladium catalyst disposed on metallic support at a temperature effective to displace said vicinal chlorides with an unsaturated linkage, wherein said metallic support comprises barium sulfate, and wherein said organic compound is selected from the group consisting of $C_2$-$C_{10}$ linear, branched, or cyclic alkyls or alkynes.

DETAILED DESCRIPTION OF PREFERRED EMBODIMENTS OF THE INVENTION

In a preferred embodiment of the invention, a method is provided for the synthesis of 2-chloropentafluoropropene via a catalytic dechlorination of 2,2,3-trichloro-1,1,1,3,3-pentafluoropropane. Preferably, the method comprises reacting 1,2,2-trichloro-1,1,3,3,3-pentafluoropropane with hydrogen in the presence of a noble metal catalyst to produce 2-chloropentafluoropropene. It has been found that these methods result in a 1,2,2-trichloro-1,1,3,3,3-pentafluoropropane conversion of at least about 50%, more preferably at least about 90%, and a selectivity for 2-chloropentafluoropropene of at least about 70 mol. %, more preferably at least about 80 mol. %.

As used herein, the term "dechlorination" with respect to vicinal chlorides means a chemical reaction wherein a pair of chlorine atoms disposed on adjacent saturated carbon atoms are removed from a compound to form an unsaturated linkage between the adjacent carbons. Although not being bound to any particular theory, applicants suggest that the dechlorination reaction mechanism involves either (1) the direct loss of the two vicinal chlorine atoms and the corresponding formation of an unsaturated linkage (followed by the reaction of $Cl_2$ with $H_2$ to produce 2HCl; or (2) replacement of one vicinal chlorine atoms for hydrogen (i.e., hydrodechlorination), followed by dehydrochlorination of the remaining vicinal sites to give the observed olefin (e.g. $CF_3CHClCF_2Cl \rightarrow CF_3CHClCF_2H \rightarrow CF_3CH=CF_2$). It is intended that both of these suggested mechanisms, as well as others, be included under the "dechlorination" rubric.

Preferred noble metal catalysts are those metals capable of exerting catalytic action under dechlorination reaction conditions as described herein, and capable of maintaining such catalytic activity for a reasonably long period of time. In certain embodiments, the catalyst may be used without any elaborate preparation process. In other embodiments, the catalysts of the present invention is activated or otherwise processed to achieve its catalytic functionality.

Preferred noble metals include metals of the platinum group, with platinum, palladium, rhodium and ruthenium being particularly preferred. In certain preferred embodiments, the metal catalyst is platinum or palladium. Combinations of two or more noble metals as catalysts can also be practiced with the present invention.

Preferably, the catalyst is bound or otherwise supported by a metallic substrate. Preferred metallic substrates include metal oxides, such as magnesium oxide, chromium oxide, aluminum oxide, and zirconium dioxide. As shown in the following examples, applicants have found that metallic supports result in a much higher selectivity compared to certain nonmetallic substrates, such as carbon. This result is unexpected, particularly in view of the prevalence of carbon as a supporting substrate for chlorination and dechlorination catalysts, including those described in U.S. Pat. No. 5,714,655 (Yamamoto, et al.) (see, e.g., Examples 1, 2, 3, and 5) and U.S. Pat. No. 3,865,885 (Bruce).

The physical structure of the substrate can be any solid form without limitation. Examples of preferred structures include meshes, pellets, and granules. The size of the support particles are not particularly limited, but is preferable from about 0.1 mm to about 10 mm in length or diameter.

When using a support, the catalytic metal is present in an amount of about 0.1 to about 10 weight percent, more preferably about 0.5 to about 5 weight percent, based upon the weight of the combined catalyst and support.

Catalyst systems comprising the catalyst and support may further comprise optional materials such as binding agents. An example of a binding agent is magnesium stearate.

The molar ratio of the reactants (hydrogen to 2,2,3-trichloro-1,1,1,3,3-pentafluoropropane) is preferably from about 0.5:1 to about 5.0:1, with at least a stoichiometric amount hydrogen based the amount of 2,2,3-trichloro-1,1,1,3,3-pentafluoropropane being preferred. More preferably, hydrogen is present in excess of the stoichiometric amount in order to facility maximum conversion. In certain embodiments, hydrogen is present in a molar ratio to 2,2,3-trichloro-1,1,1,3,3-pentafluoropropane of about 1.0:1 to about a 2.0:1, and more preferably from about 1.0:1 to about 1.5:1. In certain embodiments, the molar ratio of hydrogen to 2,2,3-trichloro-1,1,1,3,3-pentafluoropropane is less 1:1, particularly for embodiments that generate by-products recyclable as reactants or precursors of reactants of the present method.

Contact time between the hydrogen, 2,2,3-trichloro-1,1,1,3,3-pentafluoropropane, and catalyst is generally from about 0.1 seconds to about 300 seconds, but preferably is from about 1 to about 30 seconds. In certain preferred embodiments, the reaction is performed as a continuous process.

The reaction temperature is preferably from about 75° C. to about 400° C. In certain preferred embodiments, the reaction temperature is from about 150° C. to about 300° C., more preferably from about 200° C. to about 250° C. In certain other embodiments, the reaction temperature is less than about 200° C., more preferably from about 100° C. to about 150° C.

The reaction pressure is not particularly restricted. Applied pressure, reduced pressure, or atmospheric pressure may be used. For convenience and performance, atmospheric pressure or applied pressure is preferred.

In another preferred embodiment of the invention, a method is provided for reducing the number of chlorine atoms covalently bonded to an organic compound comprising the step of reacting a vicinal chloride substituted organic compound with hydrogen in the presence of a palladium catalyst disposed on metallic support at a temperature effective to replace said vicinal chlorides with an unsaturated linkage, wherein said metallic support comprises barium sulfate, and wherein said organic compound is selected from the group consisting of $C_2$-$C_{10}$ linear, branched, or cyclic alkyls.

The organic reactant preferably comprises a propane, butane, pentane or hexane backbone that, in addition to the vicinal chlorides, is substituted with at least one fluorine atom, and more preferably a plurality of fluorine atoms. The organic compound may also be substituted with additional chlorine or other halogen atoms. Examples of preferred organic compounds include, but are not limited to, the following: $CF_2C_1$—$CF_2C_1$, $CF_3$—$CCl_2$—$CF_2Cl$, $CF_3$—$CHCl$—$CClF_2$, $CF_3$—$CH_2$—$CClH$—$CClF_2$, $CF_3$—$CHCl$—$CHCl$—$CF_3$, $CF_3$—$CHCl$—$CCl_2$—$CF_3$, $CF_3$—$CH_2$—$CHCl$—$CHCl$—$CF_2Cl$, $CF_2Cl$—$CHCl$—$CH_2$—$CH$=$CF_2$ and the like. These reactants result in the following principle products in accordance with the present method: $CF_2$=$CF_2$, $CF_3$—$CCl$=$CF_2$, $CF_3$—$CH$=$CF_2$, $CF_3$—$CH_2$—$CH$=$CF_2$, $CF_3$—$CH$=$CH$—$CF_3$, $CF_3$—$CH$=$CCl$—$CF_3$, $CF_3$—$CH_2$—$CH$=$CH$—$CF_2C_1$, $CF_2$=$CH$—$CH_2$—$CH$=$CF_2$, respectively.

Optionally, the metallic support of this method includes other metallic materials including metal oxides, such as magnesium oxide, chromium oxide, aluminum oxide, and zirconium dioxide.

The physical structure of the substrate for the catalyst can be any solid form, generally without limitation. Examples of preferred structures include meshes, pellets, and granules. The size of the support particles are not particularly limited, but are preferable from about 0.1 mm to about 10 mm in length or diameter.

When using a support, the catalytic metal is present in an amount of about 0.1 to about 10 weight percent, more preferably about 0.5 to about 5 weight percent, based upon the weight of the combined catalyst and support.

Catalyst systems comprising the catalyst and support may further comprise optional materials such as binding agents. In certain preferred embodiments, magnesium stearate is used as the binding agent.

The molar ratio of hydrogen to the vicinal chloride reactant is preferably from about 0.5:1 to about 5.0:1, with at least a stoichiometric amount hydrogen based the amount of the vicinal chloride reactant being preferred. More preferably, hydrogen is present in excess of the stoichiometric amount in order to facilitate maximum conversion. In certain embodiments, hydrogen is present in stoichiometric ratio to the vicinal chloride reactant of about 1.0:1 to about 2.0:1, and more preferably from about 1.0:1 to about 1.5:1. In certain embodiments, the ratio of hydrogen to the vicinal chloride reactant is less 1:1, particularly for embodiments that generate recyclable by-products.

Contact time between the hydrogen, the vicinal chloride reactant, and the catalyst is generally from about 0.1 seconds to about 300 seconds, but preferably is from about 1 to about 30 seconds. In certain preferred embodiments, the reaction is performed as a continuous process.

The reaction temperature is preferably from about 75° C. to about 400° C. In certain preferred embodiments, the reaction temperature is from about 150° C. to about 300° C., more preferably from about 200° C. to about 250° C. In certain other embodiments, the reaction temperature is less than about 200° C., more preferably from about 100° C. to about 150° C.

The reaction pressure is not particularly restricted, and applied pressure, reduced pressure, or atmospheric pressure may be used. For convenience and performance, atmospheric pressure or applied pressure is preferred.

The following examples provide a more detailed explanation of the invention, but do no limit the scope of the invention.

EXAMPLES

Comparative Example 1

$CF_3CCl_2CF_2Cl$ Dechlorination with Pt on Carbon

A catalyst of 10 cc (4.4 g) of 0.5% Pt on 4-8 mesh carbon was prepared and dried by purging with nitrogen at 300° C. for 5 hours. The catalyst was then loaded as a bed into a quartz tube reactor having a 1.6 cm diameter. The catalyst bed was 4 to 5 cm in length.

Hydrogen and vaporized $CF_3CCl_2CF_2Cl$ were fed into the reactor at rates of 816 cc/h (36 mmol/h) and 9 g/h (38 mmol/h), respectively. Four different reaction temperatures were evaluated: 150, 200, 250 and 300° C., corresponding to residence times of 8.8 to 12 seconds. The reaction product was collected in a −78° C. cold trap after running for 30 minutes. To collect vapor samples, the cold trap was connected to a gas sample bag and allowed to warm to room temperature. The bag contents and the remaining liquid phase were then analyzed. The main product in the gas bags was $CF_3CCl{=}CF_2$ with minor amounts of $CF_3CH{=}CF_2$, but by weight, the main reaction product was the remaining liquid phase. The main components in the liquid phase were saturated materials, $CF_3CHClCF_2Cl$ (81% at 200° C. and 64% at 300° C.) and $CF_3CH_2CF_2H$ (13% at 200° C. and 15% at 300° C.). Conversions were >97% for each temperature.

Comparative Example 2

$CF_3CCl_2CF_2Cl$ Dechlorination with Pd on Carbon

The test procedure described in Comparative Example 1 was repeated, except that 10 cc (5.8 g) of 1% Pd on 4-8 mesh carbon was used as a catalyst.

At 150° C., all the product was collected in the gas bag. GC analysis indicated 61.5% $CF_3CHClCF_2Cl$ and 15.6% $CF_3CCl{=}CF_2$. At 200, 250, and 300° C., product was collected in both vapor and liquid phases (main product by weight) and had the following compositions:

|  | 200° C. | | 250° C. | | 300° C. | |
| --- | --- | --- | --- | --- | --- | --- |
|  | Vapor | Liq. | Vapor | Liq | Vapor | Liq. |
| $CF_3CH{=}CF_2$ | 2.2 | — | 13.5 | — | 19.7 | — |
| $CF_3CH_2CF_2H$ | — | 1.7 | — | 16.1 | — | 16.6 |
| $CF_3CCl{=}CF_2$ | 51.7 | 2.9 | 46.2 | — | 47.0 | 0.2 |
| $CF_3CH_2CF_2Cl$ | 8.4 | 1.2 | 15.4 | — | 7.7 | 9.5 |
| $CF_3CHClCF_2Cl$ | 33.7 | 78.9 | 7.7 | 51.9 | 13.6 | 42.3 |
| $CF_3CCl_2CF_2Cl$ | 2.3 | 10.3 | 1.7 | 6.7 | 2.7 | 5.0 |

The results show similar results for Pt and Pd supported on carbon, which produce primarily saturated products. In particular, the decrease in the amount of $CF_3CHClCF_2Cl$ with increasing temperature (liquid phase data) is consistent with the mechanism proposed by Okazaki and Habutsu in J. Fluorine Chem., 57 (1992) 191. However, rather than a corresponding increase in the amount of the expected $CF_3CCl{=}CF_2$, more reduction products, namely $CF_3CH_2CF_2C_1$ and $CF_3CH_2CF_2H$, resulted.

Comparative Example 3

$CF_3CCl_2CF_2Cl$ Dechlorination with Alumina

A catalyst of 9.1 g (9 cc) of alumina pellets with high surface area was provided and loaded as a bed into a quartz tube reactor having a 1.6 cm diameter. The catalyst bed was 4 to 5 cm in length.

Hydrogen and vaporized $CF_3CCl_2CF_2Cl$ were fed into the reactor at rates of 750 cc/h (33.6 mmol/h) and 9 g/h (37.8 mmol/h), respectively. Four different reaction temperatures were evaluated: 150, 200, 250 and 300° C. At 150 and 200° C., conversions were low, but the main product was $CF_3CCl{=}CF_2$. At 300 and 400° C., a complex mixture of products was produced.

Example 1

$CF_3CCl_2CF_2Cl$ Dechlorination with Pd on Alumina at 200° C. and 300° C.

A catalyst of 10 cc (5.8 g) of 1% Pd on ⅛ inch alumina pellets was prepared.

The test procedure described in Comparative Example 1 was repeated, with the above-mentioned except in catalyst material and that the run times were 2 to 2.5 hours and only at 200° C. and 300° C. The residence time for the reaction was approximately 10 seconds. The reaction product was collected and analyzed by a GC. The results were as follows:

| GC composition | 200° C. | 300° C. |
| --- | --- | --- |
| $CF_3CCl{=}CF_2$ | 93.2% | 81.6% |
| $CF_3CHClCF_2Cl$ | 2.2% | 5.7% |
| $CF_3CCl_2CF_2Cl$ | 0.7% | 9.5% |

As demonstrated above, the results obtained at 200 and 300° C. were dramatically different compared to the results using carbon-supported catalysts. Notably, at 300° C. and especially at 200° C., the main product is the desired olefin, namely $CF_3CCl{=}CF_2$.

Example 2

$CF_3CCl_2CF_2Cl$ Dechlorination with Pt on Alumina at 200° C.

The test procedure described in Example 1 was repeated except that the catalyst was 15 cc (6.6 g) of 0.5% Pt on ⅛ inch alumina pellets and only one reaction temperature (200° C.) was investigated. The reaction resulted in a $CF_3CCl_2CF_2Cl$ conversion of >99%, a selectivity for $CF_3CCl=CF_2$ and $CF_3CHClCF_2Cl$ of 92.2±0.4% and 5.7%±0.5%, respectively.

Example 3

$CF_3CCl_2CF_2Cl$ Dechlorination with Pd on Alumina at 150° C.

The test procedure described in Example 2 was repeated except that the catalyst was 0.5% Pd on alumina, the reaction temperature was held to approximately 150° C. and the duration of the test was approximately 12.6 hours. The mole ratio of hydrogen to $CF_3CCl_2CF_2Cl$ introduced into the quartz reactor was approximately 1.09. The reaction product was collected and its composition was determined. The reaction resulted in a conversion of $CF_3CCl_2CF_2Cl$ of about 97.8%, with a selectivity for $CF_3CH=CF_2$ of 6.8%, for $CF_3CCl=CF_2$ of 85.4%, and for $CF_3CHClCF_2Cl$ of 3.8%.

Example 4

$CF_3CCl_2CF_2Cl$ Dechlorination with Pd on Alumina at 150° C.

The test procedure described in Example 3 was repeated except that the hydrogen to $CF_3CCl_2CF_2Cl$ mole ratio was reduced to 0.84. Under these conditions, the conversion was 94%, while the selectivity for $CF_3CH=CF_2$, $CF_3CCl=CF_2$, and $CF_3CHClCF_2Cl$ was 4.9%, 89.7%, and 2.8%, respectively.

In these examples it is to be noted that both $CF_3CH=CF_2$ and $CF_3CHClCF_2Cl$ are immediate precursors to the starting material, $CF_3CCl_2CF_2Cl$. Both are converted into the starting material via chlorination, so that the yield of useful product and recyclable by-products is quite high.

Example 5

$CF_3CCl_2CF_2Cl$ Dechlorination with Pd on $BaSO_4$/Alumina at 150, 200, and 250° C.:

A catalyst prepared by grinding a mixture of 6.0 g of 5% Pd on $BaSO_4$ with 51 g alumina and then converting the resultant solid mixture into pellets. The pellets (9.0 g) were placed into a quartz reactor tube of 1.6 cm diameter to form a catalyst bed. The catalyst bed was 4.5 cm in length. The catalyst was dried overnight by heating to 300° C. with a nitrogen purge. Hydrogen (816 cc/hour or 36 mmol/h) and $CF_3CCl_2CF_2Cl$ (9 g/h or 38 mmol/h) were passed over the catalyst at 150, 200, and 250° C., for periods of 30 minutes each. GC analysis indicated >95% conversion in each case and a selectivity for $CF_3CCl=CF_2$ from 83-92%. No $CF_3CH_2CF_2H$ was produced.

Example 6

$CF_3CCl_2CF_2Cl$ Dechlorination with Pd on $BaSO_4$

A catalyst was prepared by binding 5% Pd onto roughly cylindrical pellets (0.5 cm in diameter and 0.25 cm in height) of $BaSO_4$ using 10% magnesium stearate as a binder. Approximately 10 cc (14.8 g) of the catalyst was loaded into the quartz reactor described in Example 5. Hydrogen (816 cc/hour or 36 mmol/h) and $CF_3CCl_2CF_2Cl$ (9 g/h or 38 mmol/h) were passed over the catalyst at 100 and 150° C. for periods of 30 minutes each. At 100° C., GC analysis indicated the conversion of $CF_3CCl_2CF_2Cl$ was 83.7% and the selectivity for the observed products ($CF_3CH=CF_2$, $CF_3CCl=CF_2$, and $CF_3CHClCF_2Cl$) was 6.2%, 87.0%, and 6.0%, respectively. At 150° C., the conversion improved only slightly (87.8%) and the selectivity for $CF_3CCl=CF_2$ decreased to 74.6%.

Example 7

Dechlorination of $CF_3CHClCF_2Cl$ Using Pd on Alumina

The quartz tube reactor having a 1.6 cm diameter was packed with 10 cc (14.1 g) of 0.5% Pd/alumina. Hydrogen and $CF_3CHClCF_2Cl$ were introduced into the reactor at a constant mole ratio of 1.28 and reacted at temperatures of 150, 200, 225, and 250° C. The reaction products were collected and analyzed for composition. The results of the tests showed that 1,1,3,3,3-pentafluoropropene (the apparent product of dechlorination) was formed at each temperature, but the selectivity was highest at 250° C., accounting for 82% of the product at 43% conversion.

Having thus described a few particular embodiments of the invention, it will be apparent to those skilled in the art, in view of the teachings contained herein, that various alterations, modifications, and improvements not specifically described are available and within the scope of the present invention. Such alterations, modifications, and improvements, as are made obvious by this disclosure, are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for selectively preparing 2-chloropentafluoropropene comprising reacting 1,2,2-trichloro-1,1,3,3,3-pentafluoropropane with hydrogen in the presence of a noble metal catalyst supported on metallic support to produce 2-chloropentafluoropropene, wherein said catalytic dechlorination is conducted under conditions effective to result in a 1,2,2-trichloro-1,1,3,3,3-pentafluoropropane conversion of at least about 50% and a selectivity for 2-chloropentafluoropropene of at least about 70 mol. %.

2. The method of claim 1 wherein said catalytic dechlorination is conducted under conditions effective to result in a 1,2,2-trichloro-1,1,3,3,3-pentafluoropropane conversion of at least about 90% and a selectivity for 2-chloropentafluoropropene of at least about 80 mol. %.

3. The method of claim 1 wherein said metallic support comprises barium sulfate.

4. The method of claim 1 wherein said metallic support comprises one or more metal oxides.

5. The method of claim 4 wherein said metal oxide is selected from the group consisting of magnesium oxide, chromium oxide, aluminum oxide, and zirconium dioxide.

6. The method of claim 1 wherein said noble metal catalyst is selected from the group consisting of palladium, platinum, and rhodium.

7. The method of claim 3 wherein said noble metal catalyst is selected from the group consisting of palladium, platinum, and rhodium.

8. The method of claim 5 wherein said noble metal catalyst is selected from the group consisting of palladium, platinum, and rhodium.

9. The method of claim 1 wherein said catalytic dechlorination is conducted at a temperature of about 75° C. to about 400° C.

10. The method of claim 1 wherein said catalytic dechlorination is conducted at a temperature of not more than about 200° C.

11. The method of claim 10 wherein said catalytic dechlorination is conducted at a temperature of about 100° C. to about 200° C.

* * * * *